United States Patent [19]
Chen

[11] Patent Number: 5,938,622
[45] Date of Patent: Aug. 17, 1999

[54] SAFETY VACUUM SYRINGE FOR BLOOD SAMPLING CONFORMED TO ERGONOMICS

[76] Inventor: Long-Hsiung Chen, 5F, No. 91-3, Chung Chen Road, Sec. 1, Taipei, Taiwan

[21] Appl. No.: 09/028,579

[22] Filed: Feb. 24, 1998

[30] Foreign Application Priority Data

Sep. 16, 1997 [CN] China .................................. 971169039

[51] Int. Cl.⁶ ...................................................... A61B 5/00
[52] U.S. Cl. ............................................................. 600/576
[58] Field of Search ................................... 600/573, 576, 600/577, 579, 583

[56] References Cited

U.S. PATENT DOCUMENTS

4,790,827  12/1988  Haber et al. ............................. 600/576
5,353,806  10/1994  Heinzelman et al. ................... 600/576
5,423,758   6/1995  Shaw ....................................... 600/576
5,718,239   2/1998  Newby et al. .......................... 600/576

*Primary Examiner*—Max Hindenburg
*Attorney, Agent, or Firm*—Rosenberg, Klein & Bilker

[57] ABSTRACT

A safety vacuum syringe for blood sampling conformed to ergonomics comprises: a needle head having a cannula needle with two needle tips at opposite ends held by a needle holder at a middle; a barrel having eccentric reduced front portion and a bottom opening end; an eccentric reduced lining tube inserted in the front portion of the barrel; a vacuum container having a plug sealed with front opening thereof; a tubular connector which connects the reduced lining tube to the vacuum container during using; and characteristically a reversible front cover which can be pressed into the cannula needle thoroughly in the barrel after using.

4 Claims, 8 Drawing Sheets

SAFETY VACUUM SYRINGE FOR BLOOD SAMPLING CONFORMED TO ERGONOMICS

FILED OF THE INVENTION

The present invention relates to a safety vacuum syringe for blood sampling conformed to ergonomics, and more particularly to a syringe with reversible covers which have a reversible front needle cover and a reversible bottom cover which can be inserted into the barrel respectively in a reversed manner to destroy the needle thoroughly in the barrel.

BACKGROUND OF THE INNOVATION

The present invention relates to a safety vacuum syringe for blood sampling conformed to ergonomics, and more particularly to provide a safety vacuum syringe for blood sampling conformed to health care workers and scavengers conveniently and safely.

Many diseases can be examined by a blood test, such as diabetes, hepatitis, syphilis, and AIDS. However, hepatitis, syphilis, and AIDS can be transmitted by a blood test. Hepatitis and syphilis can be cured by medicine now, but AIDS is still studying right now. Health care workers are susceptible to accidental and potentially infectious needle strikes because of the careless handing of the syringe after use. The resulting mini-accidents caused by an accidental needle strike typically require a blood test for such disease as AIDS and hepatitis. Therefore, avoiding accidental needle strike is very important for health care workers.

After finished of blood sampling, health care workers have to cover the needle cover on the needle and then withdraw in order to avoid health care workers and scavengers or further more other workers impaling themselves.

SUMMARY OF THE INVENTION

It is one object of the present invention to provide a safety vacuum syringe for blood sampling conformed to ergonomics, wherein the needle can be pulled into the barrel and thoroughly destroyed therein after using to prevent accidental needle strike.

It is another object of the present invention to provide of a safety vacuum syringe for blood sampling conformed to ergonomics, wherein the needle should be eccentrically mounted in a front portion the syringe for conforming to ergonomics.

BRIEF DESCRIPTION OF THE DRAWING

The present invention can be better understood by detailed descriptions of the following drawings, in which.

DETAILED DESCRIPTIONS OF THE INVENTION

Figure 1:
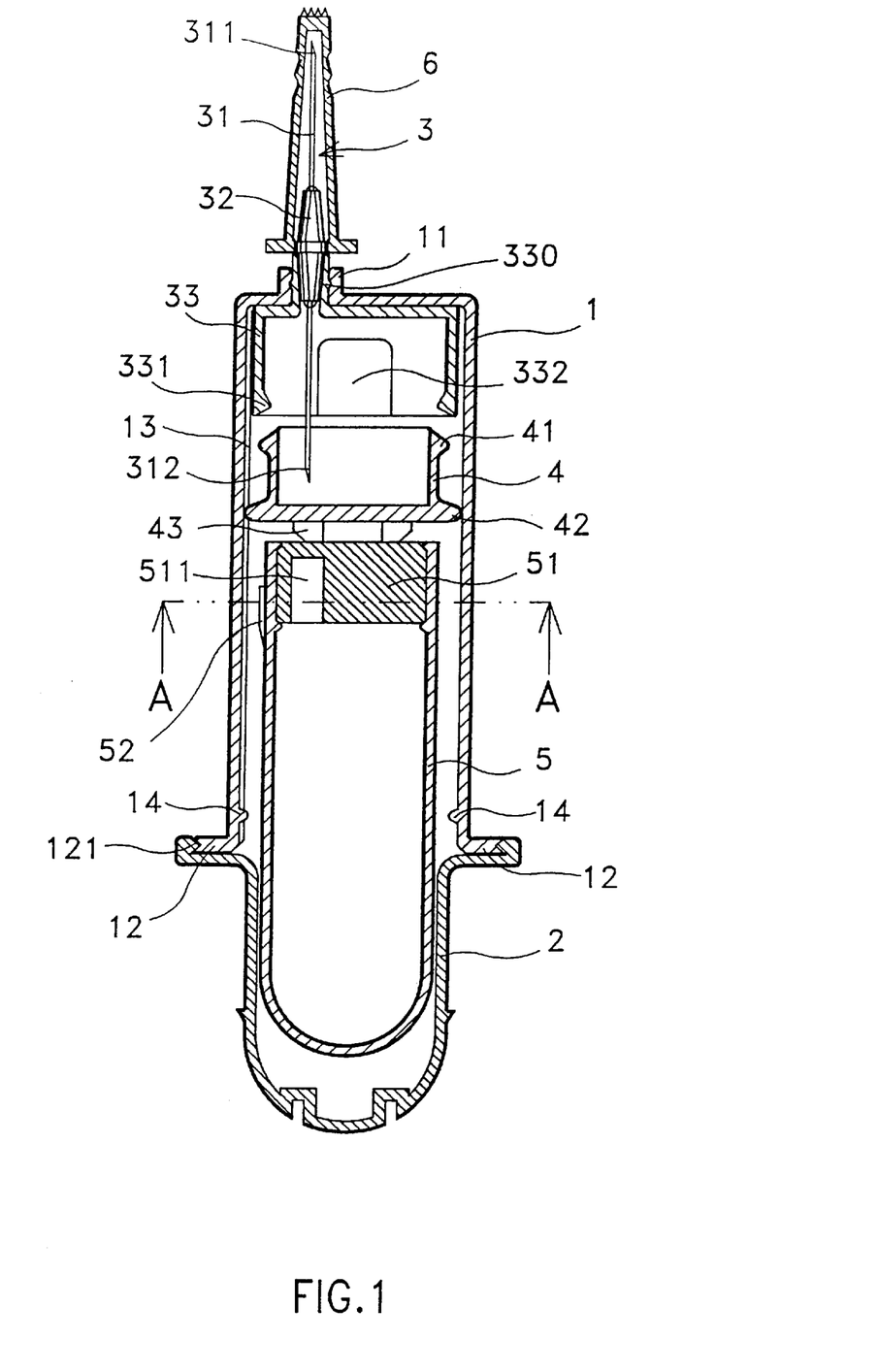
FIG. 1 is a schematics longitudinal sectional view of a preferred embodiment of the present invention before use.

Please refer to FIG. 1, which is a schematic longitudinal section view of the present invention. As shown in the FIG. 1, the present invention includes: a barrel 1 comprises a reduced inlet 11 in an eccentric front portion, an outward flange 12 disposed to a bottom opening end having a V-shaped annular glove 121 at an outer edge thereof, an inward hook-shaped flange 14 disposed on the inner wall of the barrel 1 near the bottom end and two guide strips 13 disposed on the inside of the barrel wall at one side nearest to the eccentric reduced inlet 11; a needle head 3 comprises a cannula needle 31 having an outer needle tip 311 and an inner needle tip 312 at the two opposite ends thereof, and a needle holder 32 holds the cannula needle 31 at a middle; an eccentric reduced lining tube 33 received in the front portion of the barrel 1 having a eccentric reduced portion 330 inserted in the reduced inlet 11 of the barrel 1 to receive the needle holder 32 therein, an inward teethed flange 331 disposed to a bottom of the larger portion of the reduced lining tube 33; a tubular connector 4 provided in the barrel 1 under the reduced lining tube 33 having an outward teethed flange 41 on the top which can be hooked with the inward teethed flange 331 of the reduced lining tube 33, a flange 42 disposed on the bottom edge for snapping into the barrel 1 through the inward hook-shaped flange 14 having two guide notches 421 at one side to engage with two guide strip 13 of the barrel 1, and four breakable connecting flaps 43 projected downwardly from the bottom connected with the a plug 51; a vacuum container 5 having a top opening for receiving the plug 51, the plug 51 having a crescent sectional deep cave 511 disposed to one side of the bottom surface upwardly alined with the inner needle tip 312, a reversible front cover 6 covered the outer needle tip 311, and a reversible rear cover 2 covered on the bottom flange 12 of the barrel 1.

Figure 2:
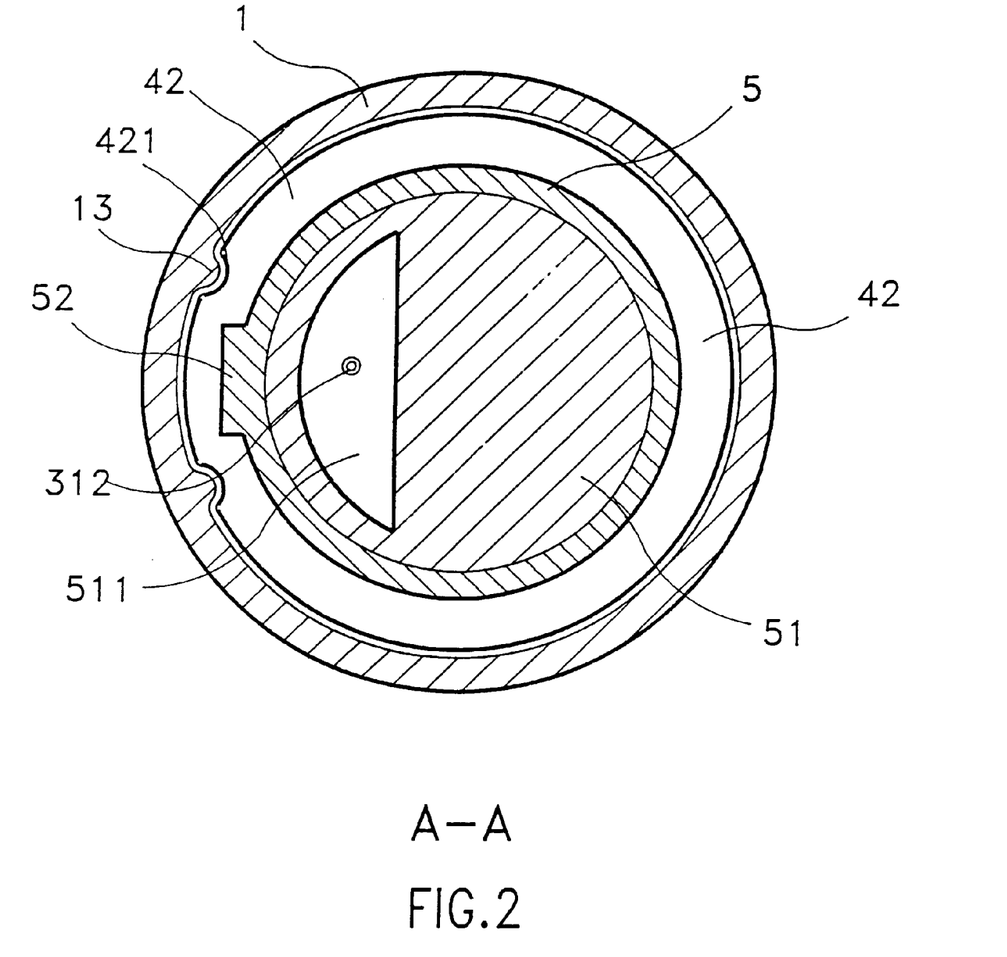
FIG. 2 is a top view of a plunger when viewed from A—A direction of FIG. 1.

Please refer to FIG. 2, which is a sectional view from A—A section line of FIG. 1. As shown in FIG. 2, the inner needle tip 312 of the needle head 3 is ready to pierce through the crescent shaped cave 511 of the plug 51. There is a projecting block 52 projected outwardly from one side of the vacuum container 5, when the vacuum container 5 and the barrel 1 are separated, the projecting block 52 can provide appropriately obstruction for the vacuum container 5 if the vacuum container 5 put on the table. Beside, the two guide notches 421 disposed on the flange 42 of the tubular connector 4 are engaged with two guides strips 13 of the barrel 1 for keeping the crescent cave 511 alined to the cannula needle 31.

Figure 3:
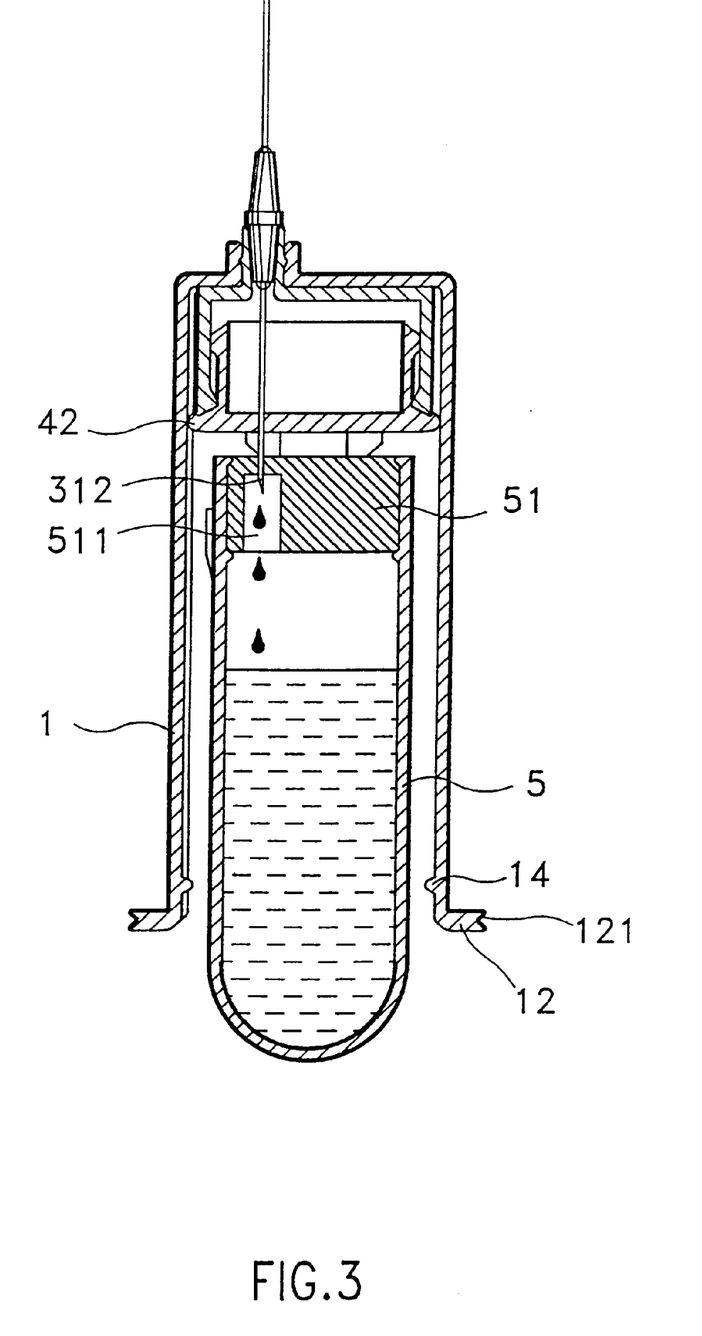
FIG. 3 is a schematics longitudinal sectional view of a preferred embodiment of the present invention during using.

Please refer to FIG. 3, which shows the syringe of the present invention in using. When the reversible front needle cover 6 and the reversible rear cover cap 2 are removed, the vacuum container 5 is pushed forward by finger so that the inner needle tip 312 of the cannula needle 31 is pierced into the vacuum container 5 through the crescent cave 511 of the plug 51 for blood sampling; simultaneously the outward teethed flange 41 of the tubular connector 4 is forced to pass through the inner teethed flange 331 into the larger portion of the reduced lining tube 33.

Figure 4:
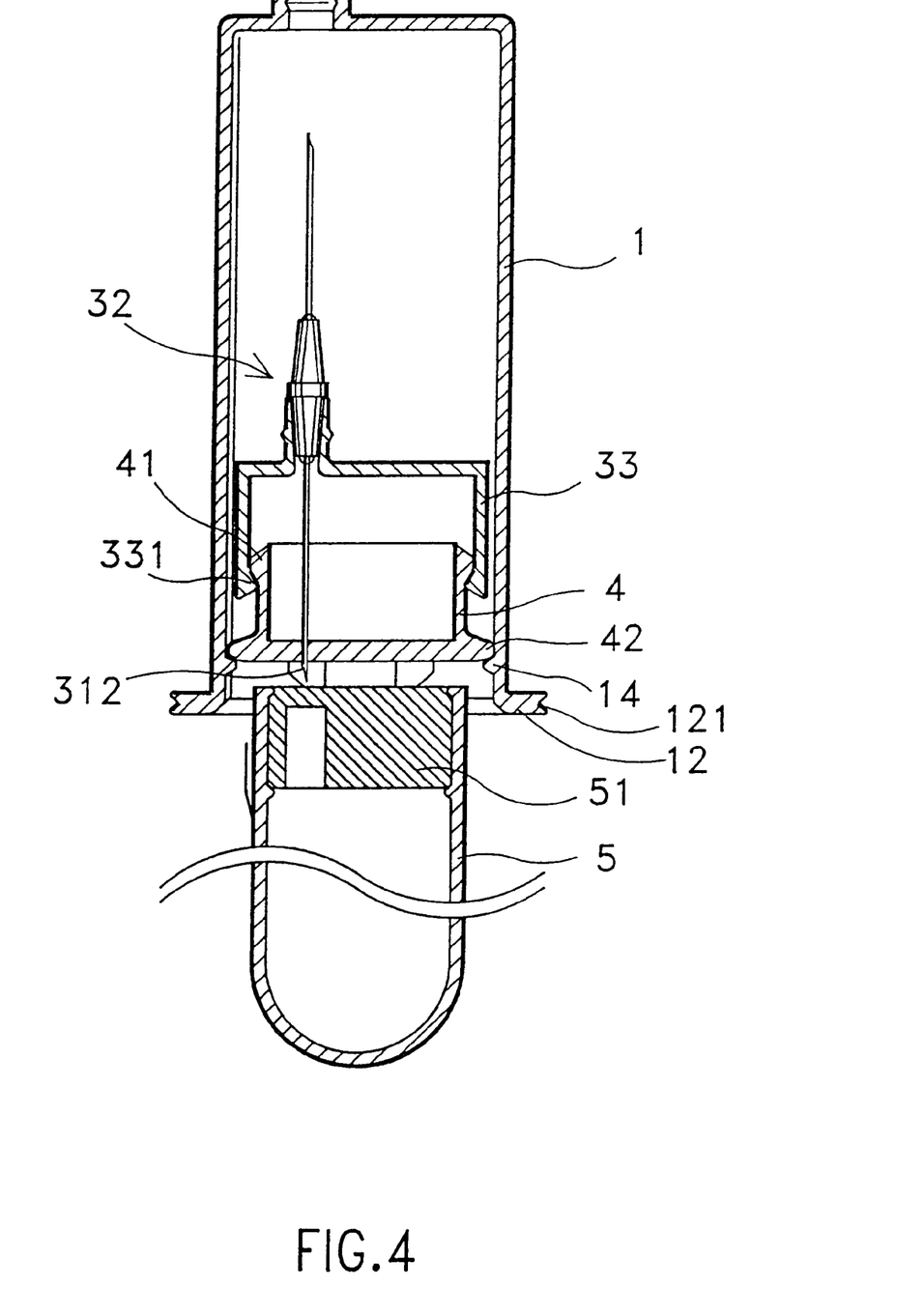
FIG. 4 is a schematics longitudinal sectional view of a preferred embodiment of the present invention after use, the needle and the tube are pulled out of the syringe.

Please refer to FIG. 4, when finished of blood sampling, the vacuum container 5 are pulled backward, the outward teethed flange 41 of the tubular connector 4 will be hooked with the inward teethed flange 331 of the reduced lining tube 33 which brings the needle head 3 including the outer needle tip 311 into the barrel 1, at the same time, the inner needle tip 312 and the plug 51 of the vacuum container 5 will be separated.

Figure 5:
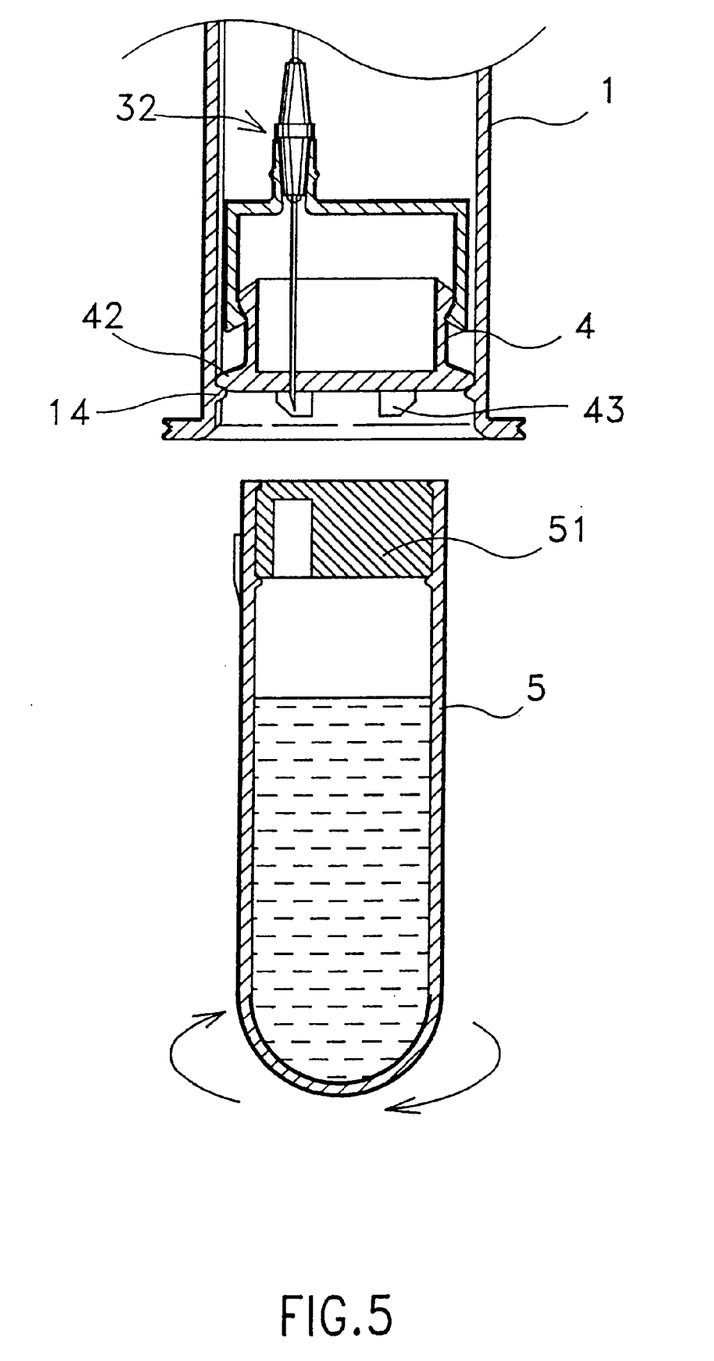
FIG. 5 is a schematics longitudinal sectional view of a preferred embodiment of the present invention when the needle and the tube are separated.

Please refer to FIG. 5, when continue pulling out of the vacuum container 5, the flange 42 of the bottom of the tubular connector 4 will be hooked with the inward hook-shaped 14 in the barrel. Four breakable connecting flaps 43 will be broken if turn round the vacuum container 5.

Figure 6:
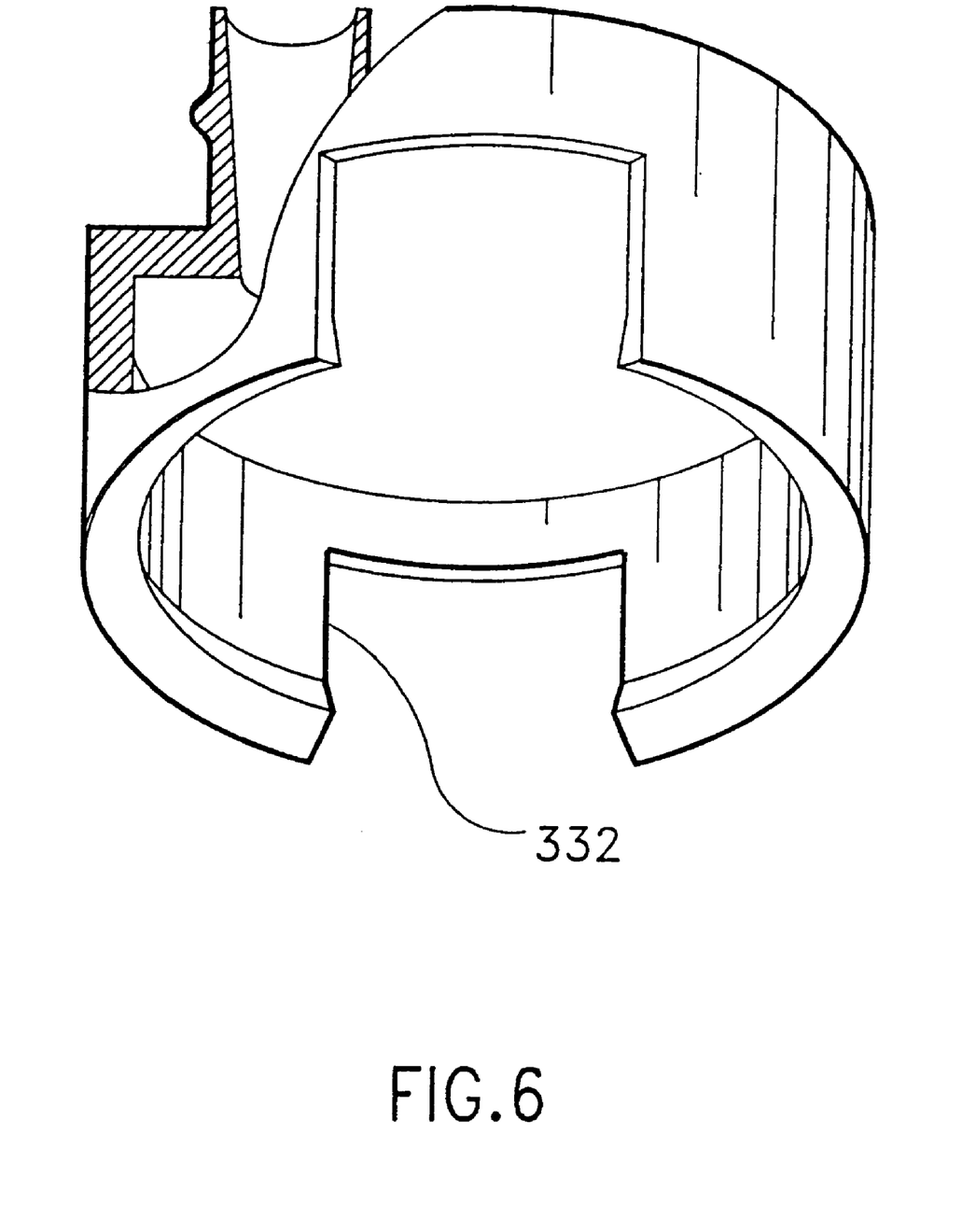
FIG. 6 is a schematics perspective sectional view of the needle of the reduced tube.

Please refer to FIG. 6, which shows a schematics perspective sectional view of the reduced lining tube 33. A plurality of slot 332 disposed on the wall of the larger potion of the reduced lining tube 33 for providing the elasticity to let the outer teethed flange 41 of the tubular connector 4 be forced thereinto and hooked therewith.

Figure 7:
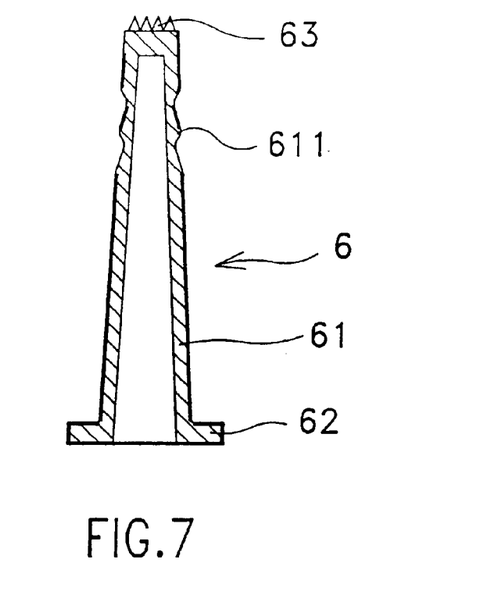
FIG. 7 is a sectional view of a reversible front cover.

FIG. 7 is a sectional view of the reversible front cover 6, which the reversible front cover 6 is formed of a tapered tube 61 having a base flange 62 disposed on a larger open end and a zigzag top plate 63 disposed in a smaller concave end, and a plurality rounds of hook-shaped rings 611 disposed on a peripheral outer surface of the tapered tube 61 at an appropriate place in which the outer diameter of the tapered tube 61 is almost equal to the inner diameter of the reduced inlet 11 of the barrel 1, so that the reversible front cover 6 can be hooked in place by one of the hook-shaped rings 611 engaged to an annular glove (not numbered) in the reduced inlet 11 of the barrel 1 while the reversible front cover 6 is inserted in a reversed manner thereinto.

Figure 8:
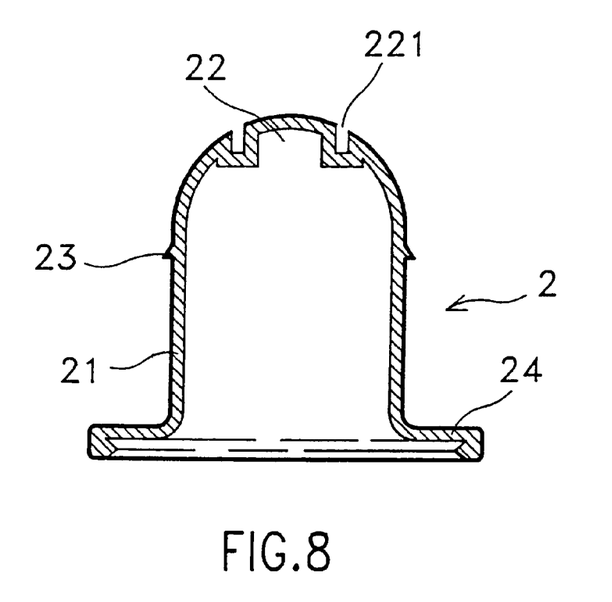
FIG. 8 is a sectional view of a reversible rear cover.

FIG. 8 is a sectional view of the reversible rear cover 2. The reversible rear cover 2 comprising a cylindrical portion 21 with an outer diameter slightly smaller than the inner diameter of barrel 1, a hollow hemisphere head 22 disposed to one end of the cylindrical portion 21 and a hook-shaped ring 23 disposed to a periphery of the cylinder portion 21 near by the root of hemisphere head 22 for snapping into the inward hook-shaped flange 14 and can be hooked therewith, an annular glove 221 concaved from the surface of the hemisphere head 22 with a radius equal to the eccentric radius of the reduced inlet 11 of the barrel 1 so as to make sure that the inner needle tip 312 will be placed into the annular glove 221 while the reversible rear cover 2 is inserted into the barrel 1 in a reversed manner.

Figure 9:
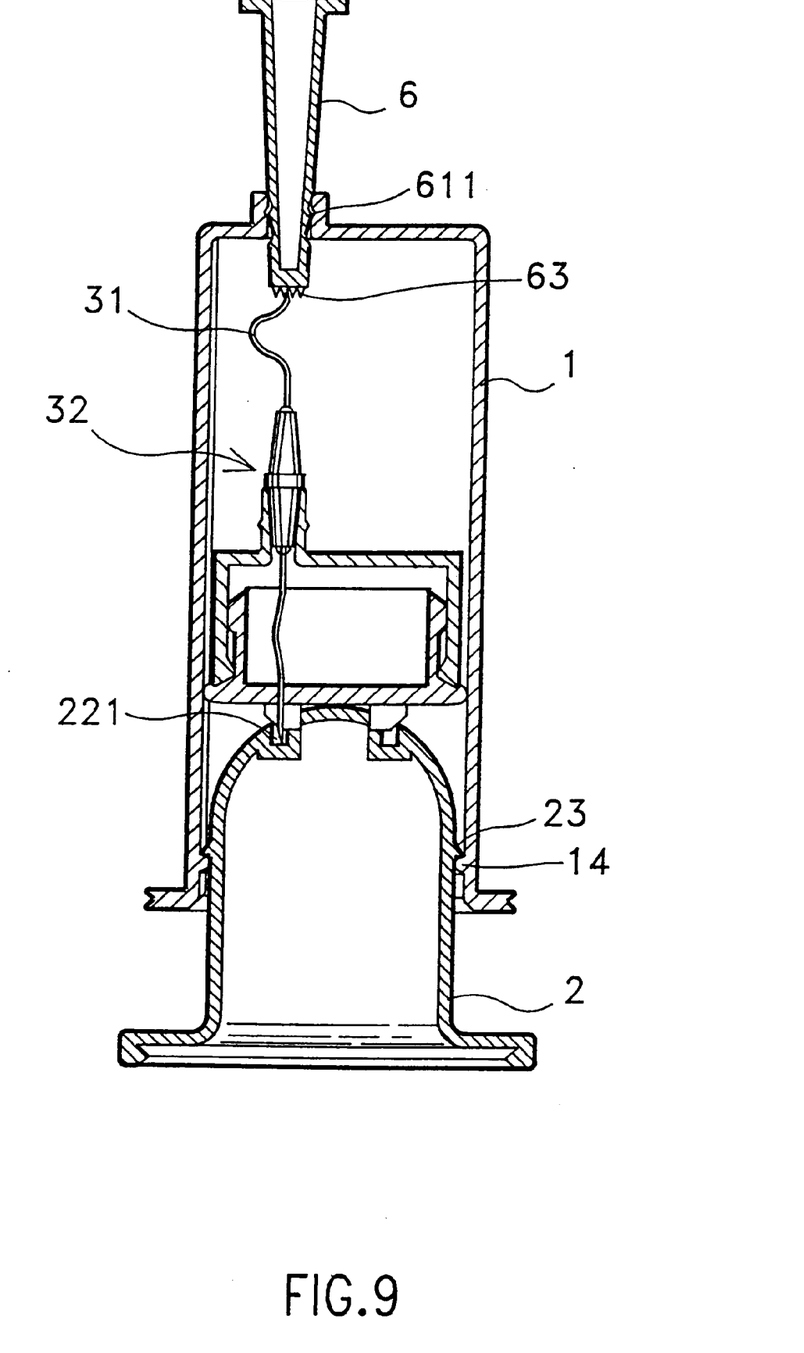
FIG. 9 is a schematic longitudinal sectional view of a preferred embodiment of the prevent invention, which the needle is destroyed and enclosed inside the barrel.

Please refer to FIG. 9, which shows the view of the present invention, wherein the needle 31 is damaged and enclosed inside the barrel 1. While the reversible front cover 6 and the reversible rear cover 2 are reversibly pressed into the barrel 1 and the cannula needle 31 will be destroyed and enclosed inside the barrel 1. Because the distance between the zigzag plate 63 of the front cover 6 and the bottom of the annular glove 221 of the reversible rear cover 2 is designed much shorter than the whole length of the cannula needle 31 in which the reversible front cover 6 is fixed in place by the engagement of hook-shaped rings 611 with the reduced inlet 11 of the barrel 1 while the reversible rear cover 2 is also fixed in place by the hook-shaped ring 23 hooked with the inward hook-shaped flange 14 of the barrel 1.

The above embodiments can be modified by any skillful person in the art without departing the spirit and scope of the accompanying claims.

What is claimed is:

1. A safety vacuum syringe for blood sampling conformed to ergonomics, comprising:

a needle head having a cannula needle with an outer needle tip and an inner needle tip respectively at opposite ends, and a needle holder to hold said cannula needle at a middle thereof;

a barrel having an eccentric reduced front portion with a reduced inlet thereat, an outward flange disposed to a bottom opening end, and two longitudinal guide strips disposed on an inside wall at one side nearest to said eccentric reduced inlet thereof;

an eccentric reduced lining tube inserted in said eccentric reduced portion of said barrel having a hook-shaped inward flange disposed at a bottom end thereof;

a vacuum container form of a cylindrical body having a front opening sealed by a plug, and a guide block disposed on an outside of said cylindrical body near said front opening thereof;

a tubular connector provided between said reduced lining tube and said vacuum container having a hook-teethed outward flange disposed to a front end, an outward flange with two guide notches disposed to a bottom end thereof, and four breakable connecting flaps extended downwardly from a bottom and connected to said plug of said container; and characteristically a reversible front cover and a reversible rear cover which can be pressed into said barrel in a reversed manner after using respectively through said reduced inlet and said bottom opening of said barrel to destroy both needle tips thoroughly in said barrel.

2. The safety syringe for blood sampling conformed to ergonomic according to claim 1 wherein said reversible front cover is formed of a tapered tube having a base flange disposed on a larger open end and a zigzag top plate disposed in a smaller concave end, and a plurality rounds of hook shaped rings disposed on a peripheral surface of said tapered tube at an appropriate place in which the outer diameter of said tapered tube is almost equal to the inner diameter of said reduced inlet of said barrel, so that the said front cover can be hooked in place by one of said hook shaped rings engaged to an annular glove in said reduced inlet of said barrel while the said front cover is pressed in a reversed manner thereinto.

3. The safety syringe for blood sampling conformed to ergonomics according to claim 1 wherein said reversible rear cover comprises a cylindrical portion with an outer diameter slightly smaller then the inner diameter of said barrel, a hollow hemisphere head disposed to one end of said cylindrical portion and an outward hook-shaped ring disposed to a periphery of said cylinder portion near by the root of said hemisphere head, an annular glove concaved from the surface of said hemisphere head with a radius equal to the eccentric radius of said reduced inlet of said barrel so as to make sure that said inner needle tip will be place into said annular while said reversible rear cover is inserted into said barrel in a reversed manner.

4. The safety syringe for blood sampling conformed to ergonomics according to claim 1 while said both reversible covers have been pressed into said barrel respectively in a reversible manner and fixed in place, in which the distance between said zigzag plate of said reversible front cover and a bottom of said annular glove of said rear cover is much shorter than the whole length of said cannula needle.

* * * * *